(12) United States Patent
Jernström et al.

(10) Patent No.: US 10,943,709 B2
(45) Date of Patent: Mar. 9, 2021

(54) 68GE/68GA GENERATOR

(71) Applicant: ITM Isotopen Technologien München AG, Garching (DE)

(72) Inventors: Jussi Jernström, Neufahrn (DE); Konstantin Zhernosekov, Munich (DE); Yury Totskiy, Munich (DE); Mark Harfensteller, Unterschleissheim (DE); Marian Meckel, Munich (DE)

(73) Assignee: ITM Isotopen Technologien München AG, Garching (DE)

( * ) Notice: Subject to any disclaimer, the term of this patent is extended or adjusted under 35 U.S.C. 154(b) by 293 days.

(21) Appl. No.: 16/073,973

(22) PCT Filed: Dec. 27, 2017

(86) PCT No.: PCT/EP2017/084627
§ 371 (c)(1),
(2) Date: Jul. 30, 2018

(87) PCT Pub. No.: WO2018/122250
PCT Pub. Date: Jul. 5, 2018

(65) Prior Publication Data
US 2019/0066860 A1    Feb. 28, 2019

(30) Foreign Application Priority Data
Dec. 27, 2016 (EP) .................. 16206969

(51) Int. Cl.
| | |
|---|---|
| G21G 4/08 | (2006.01) |
| C01G 31/02 | (2006.01) |
| C01G 33/00 | (2006.01) |
| C01G 35/00 | (2006.01) |
| G21G 1/00 | (2006.01) |
| G21G 1/10 | (2006.01) |
| G21G 4/10 | (2006.01) |
| A61K 51/00 | (2006.01) |

(52) U.S. Cl.
CPC .............. *G21G 4/08* (2013.01); *C01G 31/02* (2013.01); *C01G 33/00* (2013.01); *C01G 35/00* (2013.01); *G21G 1/0005* (2013.01); *G21G 1/10* (2013.01); *G21G 4/10* (2013.01); *A61K 51/00* (2013.01); *G21G 2001/0021* (2013.01); *G21G 2001/0094* (2013.01)

(58) Field of Classification Search
CPC . G21G 4/00; G21G 4/02; C01G 31/02; C01G 35/00
See application file for complete search history.

(56) References Cited

U.S. PATENT DOCUMENTS

| | | | |
|---|---|---|---|
| 2008/0277350 | A1 | 11/2008 | Roesch et al. |
| 2010/0202915 | A1 | 8/2010 | Zhernosekov et al. |
| 2010/0275734 | A1* | 11/2010 | Langstrom ............... B01J 41/04 75/721 |
| 2012/0325052 | A1 | 12/2012 | Rosch et al. |
| 2013/0220928 | A1 | 8/2013 | Oelsner |
| 2014/0163211 | A1 | 6/2014 | Zhernosekov et al. |
| 2016/0009742 | A1 | 1/2016 | Zhernosekov et al. |

FOREIGN PATENT DOCUMENTS

| | | |
|---|---|---|
| KR | 101646601 | 8/2016 |
| WO | 2004075819 | 9/2004 |
| WO | 2008108311 | 9/2008 |

OTHER PUBLICATIONS

International Search Report & Written Opinion dated Mar. 27, 2018 for corresponding International Application No. PCT/EP2017/084627.
Extended European Search Report dated Jul. 10, 2017 for correspondence European Application No. 16206969.4.
Search Report dated Nov. 29, 2019, for corresponding Japanese Application No. 2018-568218.

* cited by examiner

*Primary Examiner* — Michael G. Hartley
*Assistant Examiner* — Jagadishwar R Samala
(74) *Attorney, Agent, or Firm* — Lewis Kohn & Walker LLP; Kari Moyer-Henry (57) ABSTRACT

A $^{68}$Ge/$^{68}$Ga generator for a continuous production of a $^{68}$Ga daughter nuclide, wherein the $^{68}$Ge parent nuclide thereof is specifically adsorbed to an inorganic support material and wherein said $^{68}$Ge parent nuclide continuously decays to $^{68}$Ga by electron capture at a half-life of 270.82 d, wherein the inorganic support material is at least one oxide of a metal being selected from the group consisting of: Vanadium, Niobium and Tantalum. The use of at least one oxide of a metal being selected from the group consisting of: Vanadium, Niobium and Tantalum as an inorganic support material for the manufacture of a $^{68}$Ge/$^{68}$Ga generator for pharmaceutical purposes. With the inorganic support material of the present invention, it is possible to load $^{68}$Ge/$^{68}$Ga generators with up to 8000 MBq of $^{68}$Ge (corresponding to 80 µg Germanium).

10 Claims, 6 Drawing Sheets

Table of Results:

Calculation Method:       Percent

| No. | Peak-Start (min) | Peak-End (min) | Ret. Time (min) | Area | Height (mV) | Percent |
|---|---|---|---|---|---|---|
| 1 | 0.817 | 0.867 | 0.700 | 275600.0 | 333.33 | 1.725 |
| 2 | 4.333 | 4.467 | 4.433 | 158000.0 | 46.00 | 0.099 |
| 3 | 5.025 | 5.258 | 5.125 | 620000.0 | 88.00 | 0.388 |
| 4 | 5.467 | 5.658 | 5.550 | 697000.0 | 109.22 | 0.436 |
| 5 | 5.825 | 5.900 | 5.850 | 69000.0 | 25.33 | 0.043 |
| 6 | 6.017 | 6.225 | 6.042 | 730000.0 | 116.96 | 0.457 |
| 7 | 6.500 | 6.700 | 6.625 | 687702.9 | 108.59 | 0.430 |
| 8 | 6.700 | 7.342 | 6.850 | 154067300.0 | 16985.66 | 96.422 |

68GE/68GA GENERATOR

This application is a United States National Stage Application claiming the benefit of priority under 35 U.S.C. 371 from International Patent Application No. PCT/EP2017/084627 filed Dec. 27, 2017, which claims the benefit of priority from European Patent Application Serial No. EP16206969 filed Dec. 27, 2016, the entire contents of which are herein incorporated by reference.

DESCRIPTION

The present invention relates to a germanium-68/gallium-68 ($^{68}$Ge/$^{68}$Ga) generator for a continuous production of a $^{68}$Ga daughter nuclide, wherein the Ge parent nuclide thereof is specifically adsorbed to an inorganic support material and wherein said $^{68}$Ge parent nuclide continuously decays to $^{68}$Ga by electron capture at a half-life of 270.82 d. The invention further relates to the use of at least one oxide of a metal being selected from the group consisting of Vanadium, Niobium and Tantalum as an inorganic support material for the manufacture of a $^{68}$Ge/$^{68}$Ga generator, for a continuous production of a $^{68}$Ga daughter nuclide, wherein the $^{68}$Ge parent nuclide thereof is specifically adsorbed to an inorganic support material and wherein said $^{68}$Ge parent nuclide continuously decays to $^{68}$Ga by electron capture at a half-life of 270.82 d.

$^{68}$Ga is a highly attractive positron-emitting radionuclide which meanwhile plays an important role in the use of Positron Emission Tomography (PET). For a brief introduction and summary of the use of $^{68}$Ga, and in particular its chelating with DOTATOC, in diagnostics it is referred to applicant's EP 2 439 747 B1.

BACKGROUND/PRIOR ART TECHNOLOGY

In providing pure radionuclides, element-specific adsorbents are of great interest. This is also true for different fields of the chemical science. However, of special interest is the application of such materials for isolation and production of radionuclides for analytical and medical use.

A key example of the pharmaceutical application of germanium specific materials is a $^{68}$Ge/$^{68}$Ga radionuclide generator system. Such radionuclide generators are e.g. described in EP 2 216 789 A1.

The $^{68}$Ge/$^{68}$Ga radionuclide generators are based on adsorption of the radionuclide $^{68}$Ge on a germanium-specific material. Relatively long-lived $^{68}$Ge (T½=270.82 d) produces an intermediate short-lived isotope $^{68}$Ga (T½=67.6 min). While $^{68}$Ge is immobilized on a support material continuously formed $^{68}$Ga can be repeatedly eluted (produced).

$^{68}$Ga is a positron emitter ($\beta^+$ branching=89%), which can be used for preparation of radiopharmaceuticals via coordinative labelling. During the last years tumour imaging using $^{68}$Ga-labelled DOTA-conjugated peptides has become an established approach to diagnose neuroendocrine and other tumours and metastases using PET and PET/CT. A key advantage (cost, logistic advantages) in medical use of $^{68}$Ga is its availability via $^{68}$Ge/$^{68}$Ga radionuclide generators [1,2].

Essential quality parameters for $^{68}$Ge/$^{68}$Ga radionuclide generators of the prior art are undesired breakthrough of $^{68}$Ge, elution yield and elution stability of $^{68}$Ga. A limit for $^{68}$Ge breakthrough is given in the European Pharmacopoeia monograph [3] along with other parameters to measure the pharmaceutical quality of $^{68}$Ga eluate. Elution yield and elution stability of $^{68}$Ga are important factors for the efficiency and shelf life of the $^{68}$Ge/$^{68}$Ga generator. For successful radiolabelling of pharmaceuticals with $^{68}$Ga the used $^{68}$Ga preparations must satisfy high requirements to chemical and radiochemical quality. $^{68}$Ga must be produced in its "ionic" form (i.e., without any complexing agents). $^{68}$Ga preparations can be used for coordinative labelling only with low volume and low acidity. The preparation must be free from metallic impurities which are strong competitors for the incorporation of gallium into biomolecules [4-6].

The current $^{68}$Ge/$^{68}$Ga radionuclide generator systems available on the global market are based on the application of inorganic ion-exchangers or organic molecules as adsorbents (Table 1). Most commonly used inorganic ion-exchangers are $TiO_2$ (Cyclotron Company, Russian Federation and Eckert & Ziegler Isotope Products, Germany) and $SnO_2$ (iThemba Labs, South Africa). Characteristic for these generator types is contamination of $^{68}$Ga preparation with the trace of other metals from the used support materials and requirement of high acidity and/or large volume of the eluant. Thus, for the preparation of $^{68}$Ga-labelled radiopharmaceuticals utilizing the available metal oxide based radionuclide generator systems of the prior art, pre-processing of the achieved $^{68}$Ga eluate is necessary [5-8].

An alternative to inorganic ion-exchangers are organic polymers with introduced single molecules with functional groups that have a high affinity for germanium, as described in EP 2 439 747 B1. Such molecules can be pyrogallol, catechol, etc., which form strong complexes with germanium via phenolic hydroxyl groups. The key example is the only metal-free $^{68}$Ge/$^{68}$Ga radionuclide generator system on the market (ITG Isotope Technologies Garching GmbH, Germany) which is based on the application of pyrogallol-derivatized $SiO_2$ as adsorbent [7,9](Table 1). Such generators are described in detail in applicant's EP 2 439 747 B1. This prior art's $^{68}$Ge/$^{68}$Ga radionuclide generator already allows efficient radiolabelling of biomolecules without the need of pre-purification of the $^{68}$Ga eluate. However, the organic-based adsorbents applied in radionuclide generator systems are radiolytically unstable when exposed to high doses of radiation. Thus, the advanced chemical stability of the adsorbent plays the important role in developing a $^{68}$Ge/$^{68}$Ga generator for advanced performance in higher $^{68}$Ge activities.

In general, some factors related to the properties of the adsorbent of $^{68}$Ge/$^{68}$Ga generator affect on the critical quality parameters of $^{68}$Ga eluate. Low chemical stability of adsorbent increases the breakthrough of $^{68}$Ge in the conditions of high radiolytical stress. Moreover, during the shelf life of a generator $^{68}$Ge activity zone moves via elutions along the adsorbent column making germanium prone to be partly diffused inside the crystal lattice defects of metal oxides or the network of carbon chains of pyrogallol-derivatives and silica. These diffusion phenomena are likely to be factors which cause the decrease of elution yield of $^{68}$Ga via elutions being typical for the $^{68}$Ge/$^{68}$Ga generators on the market.

Taking into consideration the prior art of EP 2 439 747 B1, it is the object of the present invention to provide an improved $^{68}$Ge/$^{68}$Ga radionuclide generator which shows a negligible breakthrough of $^{68}$Ge during elution of $^{68}$Ga, which is stable to radiolysis, particularly when higher $^{68}$Ge activities are concerned, and simultaneously providing a high yield of $^{68}$Ga and finally, which is essentially of undesired impurities.

This object is achieved by a $^{68}$Ge/$^{68}$Ga generator in accordance with claim 1 and by a use of an oxide of a metal being selected from the group consisting of: Vanadium, Niobium and Tantalum as an inorganic support material for the manufacture of a $^{68}$Ge/$^{68}$Ga generator.

In particular, the present invention relates to:

a $^{68}$Ge/$^{68}$Ga generator for a continuous production of a $^{68}$Ga daughter nuclide, wherein the $^{68}$Ge parent nuclide thereof is specifically adsorbed to an inorganic support material and wherein said $^{68}$Ge parent nuclide continuously decays to $^{68}$Ga by electron capture at a half-life of 270.82 d, wherein the inorganic support material is at least one oxide of a metal being selected from the group consisting of: Vanadium, Niobium and Tantalum.

The invention further relates to a use of at least one oxide of a metal being selected from the group consisting of: Vanadium, Niobium and Tantalum as an inorganic support material for the manufacture of a $^{68}$Ge/$^{68}$Ga generator in accordance with the present invention for a continuous production of a $^{68}$Ga daughter nuclide, wherein the $^{68}$Ge parent nuclide thereof is specifically adsorbed to an inorganic support material and wherein said $^{68}$Ge parent nuclide continuously decays to $^{68}$Ga by electron capture at a half-life of 270.82 d.

A preferred embodiment of the present invention is a $^{68}$Ge/$^{68}$Ga generator in which the oxide is an oxide having the general formula (1):

$$M_2O_5 \quad (1),$$

wherein M represents Vanadium, Niobium or Tantalum.

The particularly preferred oxide used in the present invention is tantalum pentaoxide ($Ta_2O_5$), which can be used in its alpha- and/or beta-crystalline form.

The oxide used as support material in the present invention is obtainable by hydrolyzing a metal halogenide of the general formula (2):

$$MX_5 \quad (2),$$

wherein M represents Vanadium, Niobium or Tantalum; and X represents chlorine, bromine, or iodine; and converting a metal hydroxide resulting from the hydrolysis to the desired metal oxide by annealing.

It is a preferred embodiment of the present invention to use $TaCl_5$ as the metal halogenide, the hydrolysis of which resulting in $Ta(OH)_5$.

Alternatively, in accordance with the present invention, the desired oxide is also obtainable by annealing a metal powder under oxygen atmosphere, wherein said metal is selected from the group consisting of: Vanadium, Niobium and Tantalum, wherein Tantalum is preferred as metal and the resulting oxide is $Ta_2O_5$.

It is a further preferred embodiment of the present invention that the oxide particle size distribution is 5 µm to 300 µm, in particular 10 µm to 200 µm.

Typically, the $^{68}$Ge parent nuclide is adsorbed to the oxide support material in form of $^{68}$Ge(IV) cations, in particular $^{68}$Ge-aquo cations, both of which are easily available.

In accordance with a further preferred embodiment of the invention, the $^{68}$Ga is eluted from the $^{68}$Ge/$^{68}$Ga generator with 0.01 M to 0.1 M HCl, in particular with 0.05 M HCl.

It is a further preferred embodiment of the present invention that the breakthrough of $^{68}$Ge is <10$^{-3}$%, in particular <10$^{-6}$%, preferably <10$^{-7}$% at an initial activity of 1000 MBq and <4×10$^{-7}$% at an initial activity of 2000 MBq. This is far below the required European Pharmacopoeia [11] values, and far below any $^{68}$Ge/$^{68}$Ga generator available on the market (cf. Table 1 below).

Typical elution yields of $^{68}$Ga are more than 65%.

The present invention relates to the use of a novel germanium specific adsorbent, i.e. an oxide belonging to the group of metal oxides wherein the metal can be Vanadium, Niobium and Tantalum. Also mixed metal oxides or mixtures of different oxides can be used. Particularly, the pentoxides have proved to be suitable adsorbents for Ge in general and $^{68}$Ge, specifically. Although, all of the oxides from the above Vanadium group metals are generally working as specific germanium adsorbents, in practices, it has turned out that tantalum pentoxide ($Ta_2O_5$) is the most preferred one. The adsorbents in accordance with the present invention can be synthesized via a hydrolysis route from its corresponding pentachlorides, e.g. tantalum pentachloride or via an annealing route from a metal powder of V, Nb, or Ta or a mixture thereof, wherein tantalum powder is preferably used. The oxidations of the metal powders are carried out under normobaric atmospheric conditions. Pharmaceutical use of the adsorbents in accordance with the present invention allows an improved production possibility of medical positron emitting radionuclide $^{68}$Ga via a novel $^{68}$Ge/$^{68}$Ga radionuclide generator. The chemical nature of the adsorbents enable efficient adsorption of $^{68}$Ge, efficient and stable desorption of $^{68}$Ga, very low breakthrough of $^{68}$Ge and high labelling efficiency of biomolecules with $^{68}$Ga. Compared to the current systems based on other metal oxide adsorbents of the prior art, e.g. $TiO_2$ or $SnO_2$, the desired radionuclide $^{68}$Ga can be produced directly (i.e. without any pre-processing) with high chemical and radiochemical purity for preparation of $^{68}$Ga-labelled radiopharmaceuticals. Moreover, the adsorbents are chemically inert and stable against radiolysis which allows it to be successfully applied in radionuclide generators of high activities with improved performance.

Up to date, there exists no literature on the use of metal oxides of the vanadium group of the periodic table of elements, in particular, tantalum pentoxide, as adsorbent in a radiopharmaceutical radionuclide generator of the $^{68}$Ge/$^{68}$Ga type. In addition, the synthesis of the metal oxides in accordance with the present invention such as the tantalum pentoxide adsorbent by the below disclosed method is suitable for the purpose of the present invention. The achieved adsorbents underwent a thorough characterization by different solid state techniques, such as x-ray diffraction, scanning electron microscopy, Fourier-transform infrared spectrometry and surface area measurement via Brunauer-Emmet-Teller method. This encompassing analysis has yielded a well-characterized adsorbent with optimized critical parameters elutability of $^{68}$Ga, breakthrough of $^{68}$Ge, capacity of adsorbent, and labelling properties.

Table 1 below gives an outline of the $^{68}$Ge/$^{68}$Ga generators systems being currently available on the market. The last line of Table 1 shows the $^{68}$Ge/$^{68}$Ga generator according to the present invention.

TABLE 1

Specifications of the $^{68}$Ge/$^{68}$Ga generators currently available on the market.
The information in table 1 is partly taken from Roesch 2015 [10].

| Company | Adsorbent | Eluant | $^{68}$Ga elution yield | $^{68}$Ge breakthrough |
|---|---|---|---|---|
| EZAG (Obninsk)*1 | TiO$_2$ | 0.1M HCl | initial: ≈75% long term: 60% *2 | 5 × 10$^{-3}$% |
| EZAG (IGG100) | TiO$_2$ | 0.1M HCl | initial: >65% long term: >65% *2 | 10$^{-3}$% |
| iThemba Labs | SnO$_2$ | 0.6M HCl | initial: >100% *3 long term: 75% *4 | <10$^{-2}$% *3,5 |
| ITM/ITG (EP 2 439 747B1) | Pyrogallol/silica | 0.05M HCl | >80% *6 | ≤5 × 10$^{-3}$% *7 |
| Invention | Ta$_2$O$_5$ | 0.05M HCl | >65% | <10$^{-5}$% |
| Invention | V$_2$O$_5$ | 0.05M HCl | >60% | <10$^{-5}$% |
| Invention | Nb$_2$O$_5$ | 0.05M HCl | >60% | <10$^{-5}$% |

*1 Provided by Cyclotron Co. Ltd, Obninsk, Russia
*2 After 200 elutions
*3 Expressed as ratio of radioactivities of $^{68}$Ge/$^{68}$Ga in the eluate
*4 After 300 days
*5 Values true for daily elutions only
*6 On calibration date in 4 mL 0.05M HCl
*7 $^{68}$Ge content in $^{68}$Ga at calibration time

DETAILED DESCRIPTION

The present invention relates to the use of novel germanium specific adsorbents being selected from the group of vanadium oxide, niobium oxide and tanatalum oxide, particularly tantalum pentoxide (Ta$_2$O$_5$) in a $^{68}$Ge/$^{68}$Ga radionuclide generator. The chemically inert and stable adsorbents enable efficient adsorption of $^{68}$Ge, efficient and stable desorption of $^{68}$Ga, very low breakthrough of $^{68}$Ge and efficient labelling of biomolecules with $^{68}$Ga.

Further features and advantages of the present invention will become evident from the following description of examples as well as from the drawings.

EXAMPLE 1: GENERATORS UP TO 1000 MBQ (27 MCI)$^{68}$GE

The following synthesis method is described by way of example for the manufacture of tantalum pentoxide as the most preferred metal oxide in accordance with the present invention. However, those having average skill in the art will understand that the present synthesis method easily can be applied to the manufacture of the other preferred embodiments of the present invention, namely vanadium pentoxide and niobium pentoxide, particularly due to their close chemical properties.

Synthesis of Ta$_2$O$_5$

A synthesis method for the Ta$_2$O$_5$ adsorbent was developed by the applicant using two primary synthesis routes: hydrolysis route using tantalum pentachloride (TaCl$_5$) as a starting material and annealing route using tantalum powder (Ta powder) as a starting material.

Hydrolysis Route

Hydrolysis of TaCl$_5$ was performed in water using controlled water/TaCl$_5$ ratio. Temperature of water during the hydrolysis process was adjusted and kept stable in order to control the particle size of the final product Ta$_2$O$_5$. Annealing temperature of the tantalum hydroxide (Ta(OH)$_5$) was chosen based on the solid phase investigations in order to find the best performance for the adsorbent applied in a $^{68}$Ge/$^{68}$Ga radionuclide generator.

Annealing Route

Oxidation of Ta powder was performed with starting material with selected particle size distribution. Annealing temperature of the Ta powder was chosen based on the solid phase investigations in order to find the best performance for the adsorbent applied in a $^{68}$Ge/$^{68}$Ga radionuclide generator.

Specifications of Synthesized $Ta_2O_5$

The specifications of the synthesized $Ta_2O_5$ applied in the radiopharmaceutical $^{68}$Ge/$^{68}$Ga generator include the following criteria: annealing temperature, particle size distribution, distribution factor between $^{68}$Ge and adsorbent ($K_D$), and desorption (elutability) of $^{68}$Ga. The criteria are summarized in Table 2 below.

TABLE 2

Specifications of synthesized $Ta_2O_5$.

| Specification | Criterium |
| --- | --- |
| Annealing temperature | 600-1350° C. |
| Distribution factor ($K_D$) | 2000-20000 mL/g |
| Elutability of $^{68}$Ga | ≥65% |
| Particle size distribution | 10-200 μm |

Characterization of $Ta_2O_5$ Adsorbent

Figure 4A:
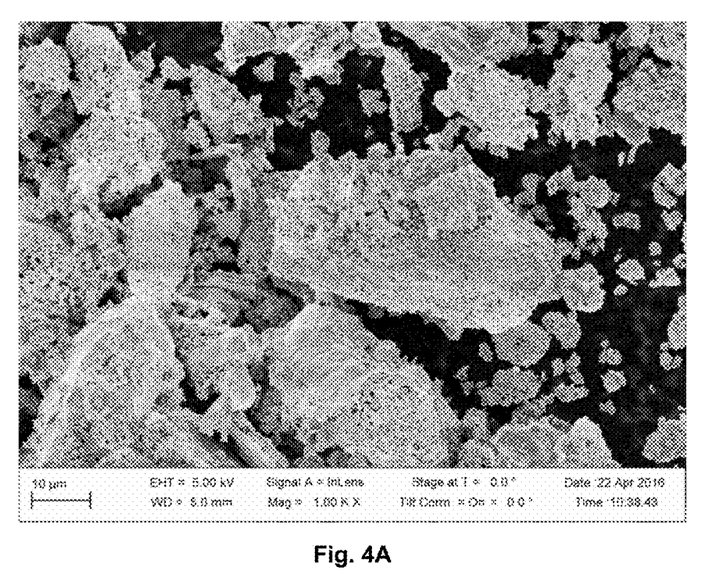
FIG. 4A and FIG. 4B are images presenting scanning electron microscope (SEM) images of the surface structure of β-Ta$_2$O$_5$ (FIG. 4A) and α-Ta$_2$O$_5$ (FIG. 4B). From the images one can see the different surface characteristics indicating higher surface area of β-Ta$_2$O$_5$ (FIG. 4A) suggesting higher capacity when applied in a $^{68}$Ge/$^{68}$Ga generator column.
Figure 4B:
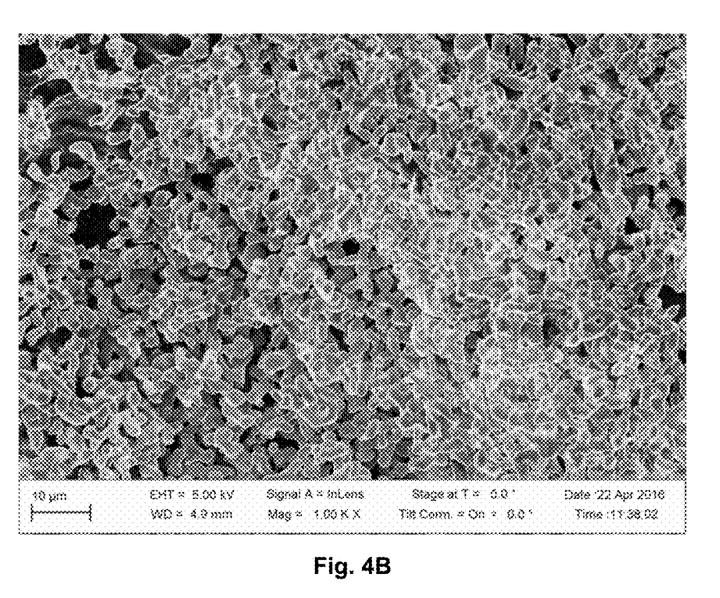
Figure 5:
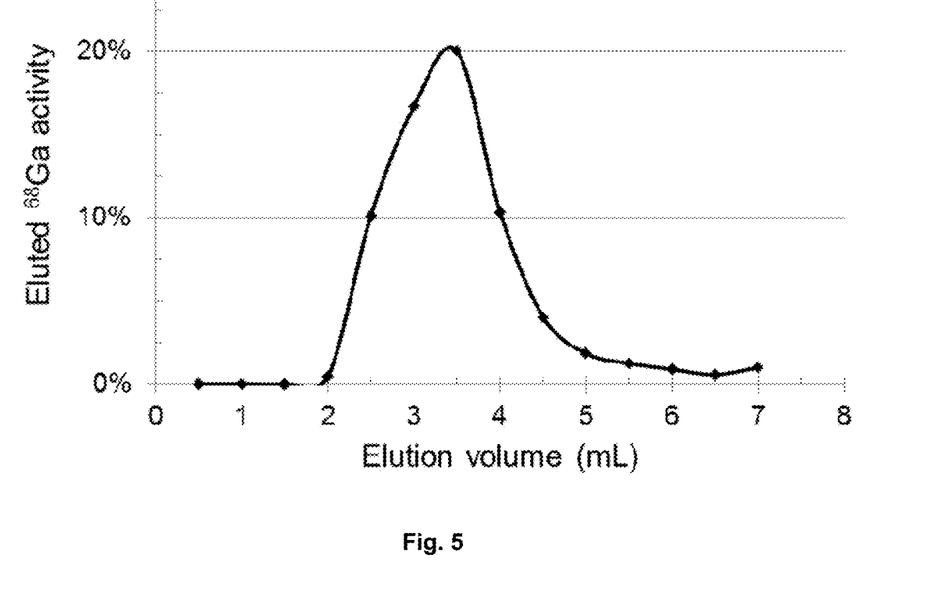
FIG. 5 represents an elution profile of $^{68}$Ga of a $^{68}$Ge/$^{68}$Ga generator applied with Ta$_2$O$_5$ adsorbent. Initial $^{68}$Ge activity of the generator was 1000 MBq.

During the development of synthesis of the tantalum pentoxide adsorbent different parameters correlating to adsorption and desorption properties of $^{68}$Ge and $^{68}$Ga, respectively, were investigated (Table 3). These parameters included crystal structure and surface morphology of the $Ta_2O_5$, surface area and particle size distribution. The results obtained by radiochemical analysis for $^{68}$Ge (distribution factor ($K_D$) and capacity) and for $^{68}$Ga (elutability) were correlated by the observations and results obtained by analytical techniques such as x-ray diffraction (XRD) applied for crystal structure analysis, scanning electron microscopy (SEM) (FIG. 4) applied for surface morphology investigations, surface area determination (Brunauer-Emmet-Teller (BET)) and determination of particle size distribution.

TABLE 3

Correlation between the different specifications of the synthesized $Ta_2O_5$ adsorbent material.

| Adsorbent | Annealing temperature (° C.) | Particle size distribution (μm) | $K_D$ for $^{68}$Ge (mL/g) | Elutability of $^{68}$Ga |
| --- | --- | --- | --- | --- |
| β-$Ta_2O_5$ | 800-1350 | 10-200 | 137992-240964 | 7.2% |
| | | | 101219-140377 | 37% |
| | | | 18691-19522 | 47% |
| | | | 7878-8905 *¹ | 69% *¹ |
| α-$Ta_2O_5$ | 1500 | 10-200 | 779-870 | 67% |
| | | | 567-615 | 68% |

*¹ Particles of <8 μm diameter separated

Tetravalent germanium exists in generator-relevant solution pH (0.05 M HCl) and Ge concentrations ([$Ge_{total}$]<0.005 M) in the form of germanic acid ($Ge(OH)_4$) [12,13]. In these conditions germanium binds with hydroxyl groups on the surface of tantalum pentoxide [14]. Experiments have indicated a clear positive correlation between small particle size and high surface area to efficient adsorption of $^{68}$Ge. On the other hand, small particle size has a negative effect on the efficiency of elutability of $^{68}$Ga. That is why the main goals in the development of the synthesis method for $Ta_2O_5$ have been to minimize the formation of small particles (<10 μm), and to increase the surface area of $Ta_2O_5$ particles. In the FIG. 4 one can see the difference in the surfaces of the two crystalline forms of $Ta_2O_5$: the particles formed of β-$Ta_2O_5$ (FIG. 4A) have surface covered with caves and formations formed during the aggressive chemical conditions of hydrolysis; thus providing higher surface area and higher $K_D$ and capacity for $^{68}$Ge compared to the particles of α-$Ta_2O_5$ (FIG. 4B) where these morphological structures have "melted" due to high annealing temperature. On the other hand, the glossy surface characteristics of the α-$Ta_2O_5$ effects provide better elutability properties for $^{68}$Ga.

In conclusion: the aim has been to develop a method of synthesis for $Ta_2O_5$ adsorbent with the ideal equilibrium between efficient adsorption of $^{68}$Ge (shelf life) and efficient elutability of $^{68}$Ga (elution yield).

A batch of germanium specific adsorbent was synthesised by following the hydrolysis route:

Tantalum pentachloride ($TaCl_5$) was mixed with hot water (80° C., solid/liquid ratio 20 g/L) to produce tantalum hydroxide ($Ta(OH)_5$), which was annealed under 900° C. over 24 h in order to form crystalline tantalum oxide ($Ta_2O_5$). After isolation of particles with a size range of 10 μm-200 μm the final material was used as an adsorbent for the $^{68}$Ge/$^{68}$Ga generators.

Two generator columns were filled with a known amount of the adsorbent (8 g). The columns were loaded with a known amount of $^{68}$Ge (1000 MBq, 2000 MBq) and stable Ge (total mass of Ge=80 μg). The radionuclide generators were produced under GMP-conditions.

The $^{68}$Ge/Ga generators were subjected to an elution program and the critical parameters were followed. At the current stage of the elution program the following values related to the critical parameters are valid:

Current total cumulative elution volume: 700 mL (1000 MBq), 400 mL (2000 MBq)
Elution yield of $^{68}$Ga: >65%, stable
Currently: 70% (1000 MBq), 73% (2000 MBq) (FIG. 2)
Elution volume: 6 mL (FIG. 6)
Breakthrough of $^{68}$Ge: <10$^{-6}$% (level of Ph. Eur.: 10$^{-3}$%)
Currently: 10$^{-7}$% (1000 MBq), 4×10$^{-7}$% (2000 MBq) (FIG. 1)
Labelling efficiency: >96% after 90 h of ingrowth period via direct elution ($^{68}$Ga-DOTA-TOC) (FIG. 3).

Critical Quality Parameters: Breakthrough of $^{68}$Ge and Elution Yield of $^{68}$Ga In general, some factors related to the properties of the adsorbent of $^{68}$Ge/$^{68}$Ga generator affect on the critical quality parameters of $^{68}$Ga eluate. Low chemical stability of adsorbent increases the breakthrough of $^{68}$ in the conditions of high radiolytical stress. Moreover, during the shelf life of a generator $^{68}$Ge activity zone moves via elutions along the adsorbent column making germanium prone to be partly diffused inside the crystal lattice defects of metal oxides or the network of carbon chains of pyrogallol-derivatives and silica. These diffusion phenomena are likely to be factors which cause the decrease of elution yield of $^{68}$Ga via elutions being typical for the prior art $^{68}$Ge/$^{68}$Ga generators on the market.

Figure 1:
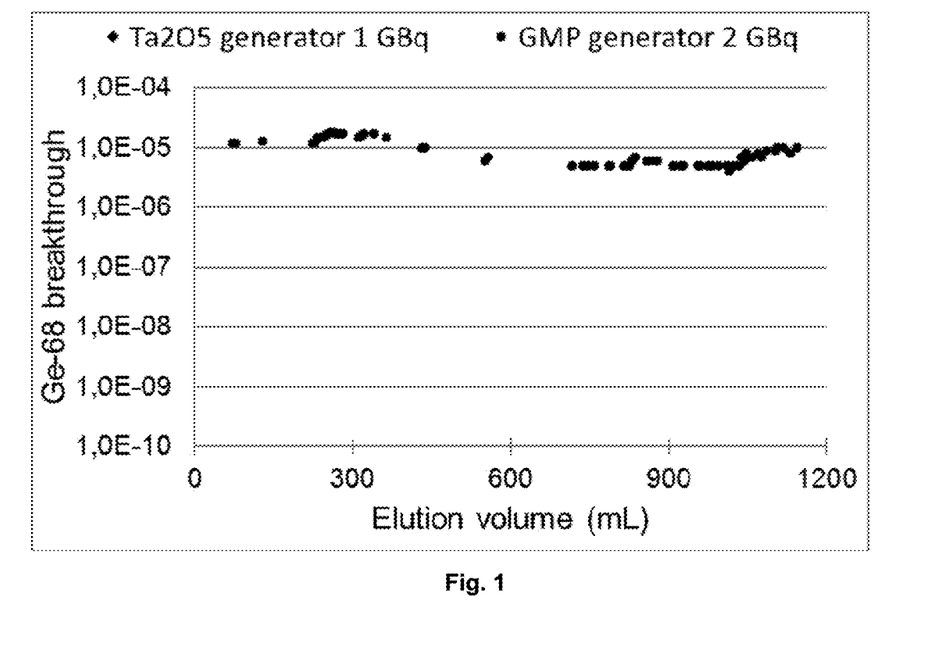
FIG. 1 is a graphical representation of the percentage of breakthrough of $^{68}$Ge as a function of cumulative elution volume of two $^{68}$Ge/$^{68}$Ga generators. Comparison between the current ITG GMP generator according to EP 2 439 747 B1 and the Ta$_2$O$_5$-based generator according to the present invention shows the significant difference in the levels of breakthrough of $^{68}$Ge.

Tantalum pentoxide was originally chosen to be used as adsorbent for two main reasons: It is chemically inert and stable material, which makes it suitable to be applied in conditions of high radiolysis and surprisingly yielding low breakthrough of $^{68}$Ge (FIG. 1). Moreover, the fact that the tantalum cation is (primarily) in pentavalent oxidation state was regarded to be beneficial for the $^{68}$Ga elution yield stability and preventative against the diffusion of tetravalent germanium into the crystal lattice of the $Ta_2O_5$ (FIG. 2).

Figure 2:
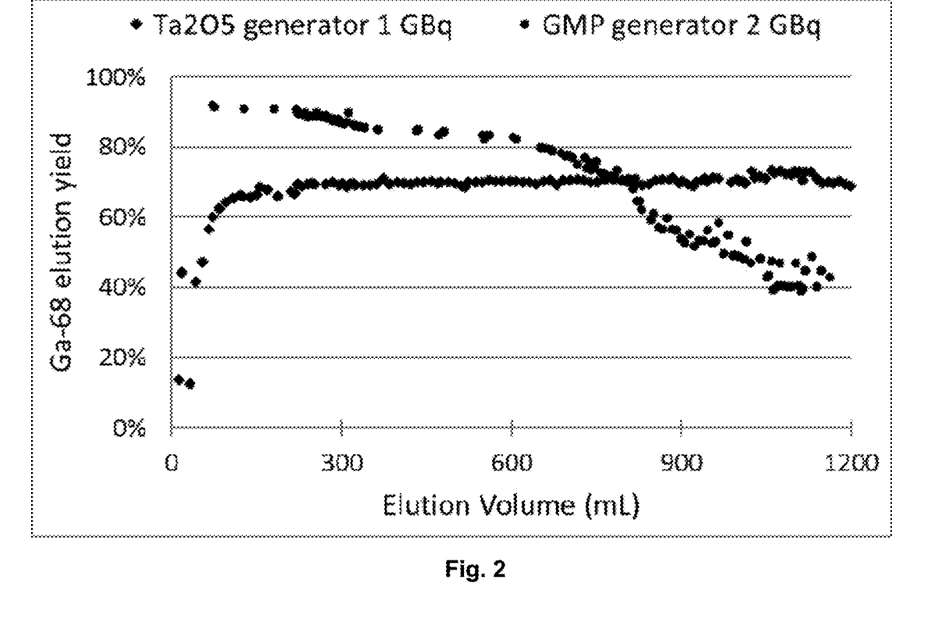
FIG. 2 is a graphical representation of the elution yield of $^{68}$Ga as a function of cumulative elution volume of two $^{68}$Ge/$^{68}$Ga generators. Comparison between the current ITG GMP generator according to EP 2 439 747 B1 and the Ta$_2$O$_5$-based generator of the present invention shows a large difference in the stability of elution yield of $^{68}$Ga.
Figure 3:
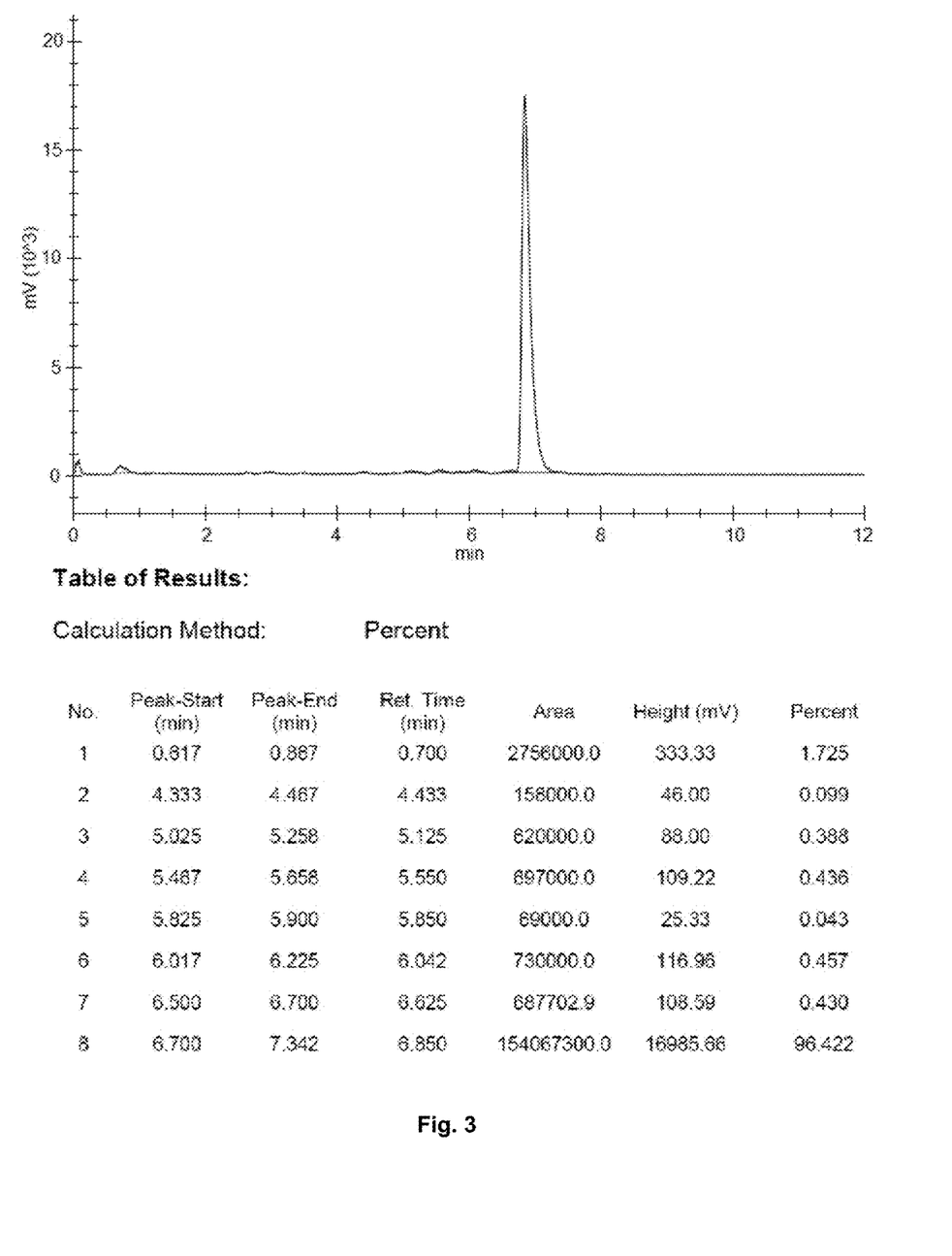
FIG. 3 shows an HPLC chromatogram presenting the results from direct labelling with $^{68}$Ga after 90 h of ingrowth time of a 1900 MBq $^{68}$Ge/$^{68}$Ga generator. The percentages of free non-labelled $^{68}$Ga and labelled $^{68}$Ga are 1.73% and 96.42%, respectively.

Evidence of these properties, i.e., chemical stability and nature can be seen in the FIGS. 1 and 2 presenting the behavior of breakthrough of $^{68}$Ge and elution yield of $^{68}$Ga in the GMP generator and Ta$_2$O$_5$ generator in function of cumulative elution volume, respectively.

Critical Quality Parameter: Labelling Properties of Generator

Labelling properties of a radiopharmaceutical $^{68}$Ge/$^{68}$Ga generator applied with synthesized Ta$_2$O$_5$ adsorbent were tested by a method based on the monograph of European Pharmacopoeia [11]. The test was performed for $^{68}$Ga eluate eluted from a generator with the nominal $^{68}$Ge activity of 1900 MBq and ingrowth time (time of no elutions) of 90 hours. The aim of the test was to demonstrate the stability of the Ta$_2$O$_5$ adsorbent against radiolysis even during a longer period of time of no elutions. The results obtained by high-pressure liquid chromatography (HPLC) from the direct labelling were over 96% yield of labelled product. This clearly demonstrates the extensive stability of the Ta$_2$O$_5$ adsorbent used in a $^{68}$Ge/$^{68}$Ga generator, and indicates that no rinsing after weekends is necessary in order to yield a fully functional generator for the use of radiolabelling (FIG. 3).

EXAMPLE 2: GENERATORS GREATER THAN 1850 MBQ (50 MCI) $^{68}$GE

Figure 6:
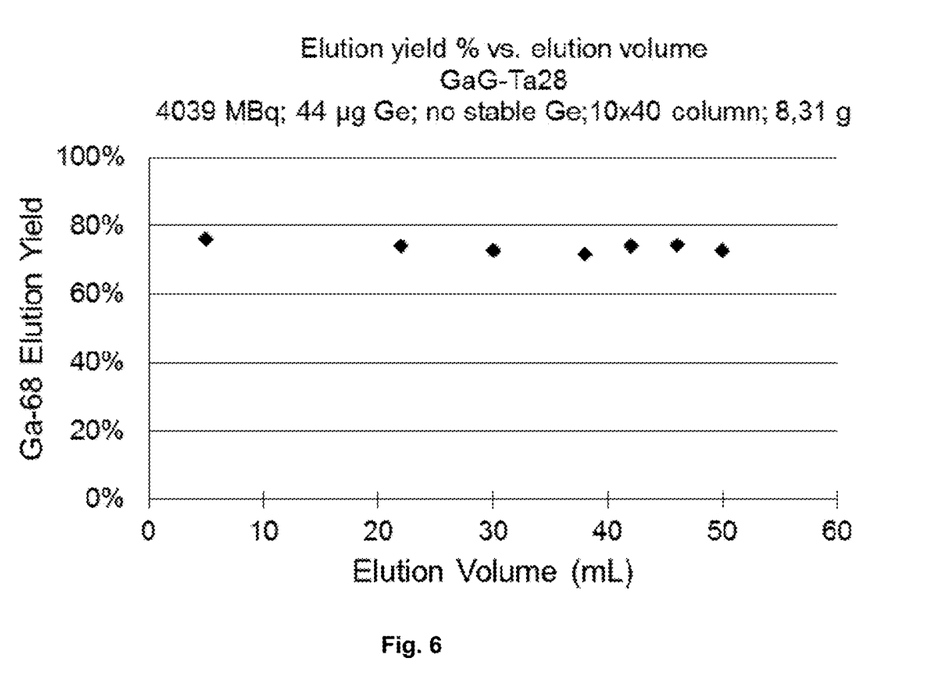
FIG. 6 represents a diagram of elution yield vs. elution volume of $^{68}$Ga elution yields showing results greater than 70% (3 000 MBq)

Generator column was filled with known amount of the adsorbent (8-9 g). The column was loaded with known amount of $^{68}$Ge (4000 MBq) and no stable Ge was added (total amount of Ge was calculated by specific activity of Ge-68 to 44 µg). The $^{68}$Ge/$^{68}$Ga generator was subjected to an elution program and the critical parameters were followed. At the current stage of the elution program the following values related to the critical parameters are shown in FIGS. 6, 7, and 8:

In particular, FIG. 6 shows a diagram in which values of elution yield in % are plotted against the elution volume in ml, showing $^{68}$Ga elution yields of greater than 70% (3000 MBq).

Figure 7:
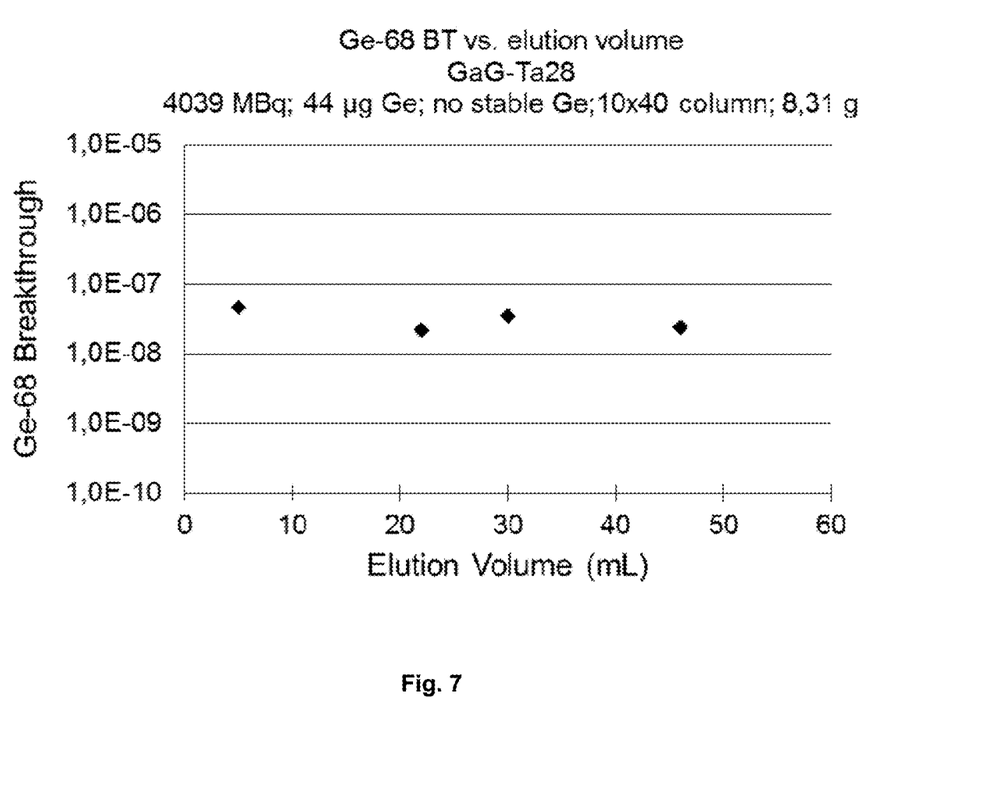
FIG. 7 represents a diagram of $^{68}$Ge breakthrough, wherein values are below 10$^{-7}$%.

FIG. 7 shows that the breakthrough values for $^{68}$Ge are less than 10$^{-7}$%.

Figure 8:
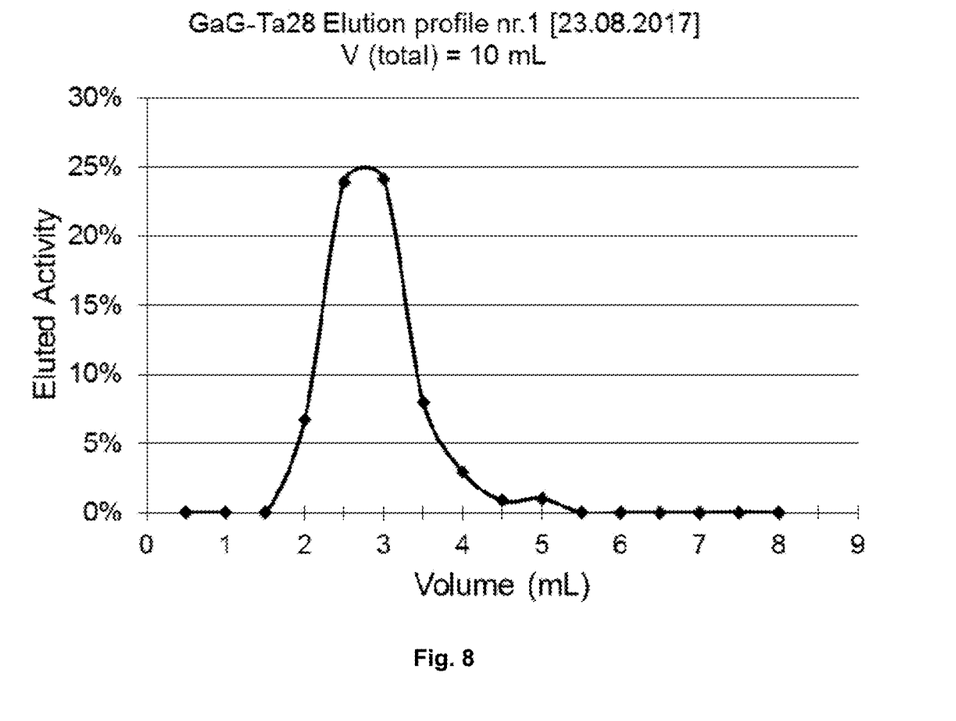
FIG. 8 represents an elution profile of $^{68}$Ga of a $^{68}$Ge/$^{68}$Ga generator applied with Ta$_2$O$_5$ adsorbent. Initial $^{68}$Ge activity of the generator was 4 000 MBq.

Finally, FIG. 8 represents an elution profile of $^{68}$Ga of a $^{68}$Ge/$^{68}$Ga generator applied with the Ta$_2$O$_5$ adsorbent. The initial $^{68}$Ge activity of the generator was 4000 MBq.

The Generator showed $^{68}$Ga yields >3000 MBq. Typical Labelling procedures with common $^{68}$Ga PET tracers, such as PSMA-11 (HBED-CC) and DOTATATE showed results of 55 mCi ([Ga-68]Ga-HBED-CC) and 45 mCi ([Ga-68]Ga-DOTATATE) at end of Production (end of production is typically 30 min to 60 min after Generator elution).

Based on calculation of the specific activity of 100 GBq/mg $^{68}$Ge and the nominal total applicable Germanium amount on 8-9 g Ta$_2$O$_5$ Generator columns, it is possible to load generators with 8000 MBq of $^{68}$Ge (corresponds to 80 µg Germanium).

Similar elution profiles, breakthrough values, yields (data not shown) as specified in Examples 1 and 2 could be achieved when replacing the Ta$_2$O$_5$ by its corresponding oxides Nb$_2$O$_5$ and V$_2$O$_5$. The synthesis thereof follows essentially the same routes as described in Example 1 above.

With the present invention, the clinical demand of a radiopharmaceutical grade $^{68}$Ga in sufficient quantity and reliable quality can be fulfilled.

REFERENCES

[1] Al-Nahhas A, Win Z, Szysko T, Singha A, Nannil C, Fanti S, Rubello D. Gallium-68 PET: A new frontier in receptor cancer imaging. Anticancer Res. 2007; 27: 4087-4094.

[2] Maecke H, Hofmann M, Haberkornm U. $^{68}$Ga-labeled peptides in tumor imaging. J Nuc Med. 2005; 46: 172S-178S.

[3] Gallium ($^{68}$Ga) chloride solution for radiolabelling. Ph. Eur. 7.8. 07/2013:2464; 5643-5644.

[4] Breeman W, Jong M, Blois E, Bernard B, Konijnenberg M, Krenning E. Radiolabelling DOTA-peptides with $^{68}$Ga. Eur J Nuc Med Mol Imaging. 2005; 32: 478-485.

[5] Meyer G-J, Mäcke H, Schuhmacher J, Knapp W, Hofmann M. $^{68}$Ga-labelled DOTA-derivatised peptide ligands. Eur J Nuc Med Mol Imaging. 2004; 31: 1097-1104.

[6] Zhemosekov K, Filosofov D, Baum R, Aschoff P, Bihl H, Razbash A, Jahn M, Jennewein M, Rösch F. Processing of generator-produced $^{68}$Ga for medical application. J Nuc Med. 2007; 48: 1741-1748.

[7] Zhemosekov K, Nikula T. Molecule for functionalizing a support, attachment of a radionuclide to the support and radionuclide generator for preparing the radionuclide, and preparation process. Patent US 2010/0202915 A1.

[8] Chakravarty R, Chakraborty S, Ram R, Vatsa R, Bhusari P, Shukla J, Mittal B R, Dash A. Detailed evaluation of different $^{68}$Ge/$^{68}$Ga generators: an attempt toward achieving efficient $^{68}$Ga radiopharmacy. J Label Compd Radiopharm. 2016; 59: 87-94.

[9] Schuhmacher J, Maier-Borst W. A new $^{68}$Ge/$^{68}$Ga radioisotope generator system for production of $^{68}$Ga in dilute HCl. J Appl Rad Isotopes. 1981; 32: 31-36.

[10] Roesch F. $^{68}$Ga radiopharmaceuticals: Current status and future. In: International conference on clinical PET-CT and molecular imaging (IPET 2015). Vienna, Austria, 5-9 Oct. 2015.

[11] Gallium ($^{68}$Ga) edotreotide injection. PA/PH/Exp. 14/f (07) 12 ANP; E1-E7.

[12] Baes C F, Mesmer R E. The hydrolysis of cations. Robert E Krieger Publishing Company, Malabar, Fla., USA. 1986.

[13] Wood S A, Samson I M. The aqueous geochemistry of gallium, germanium, indium and scandium. Ore Geol Rev. 2006; 28: 57-102.

[14] Pokrovsky O S, Pokrovski G S, Schott J, Galy A. Experimental study of germanium adsorption on goethite and germanium coprecipitation with iron hydroxide: X-ray absorption fine structure and macroscopic characterization. Geochim Cosmochim Ac. 2006; 70: 3325-3341.

The invention claimed is:

1. A $^{68}$Ge/$^{68}$Ga generator for a continuous production of a $^{68}$Ga daughter nuclide, wherein the $^{68}$Ge parent nuclide thereof is specifically adsorbed to an inorganic support material and wherein said $^{68}$Ge parent nuclide continuously decays to $^{68}$Ga by electron capture at a half-life of 270.82 d, characterized in that
the inorganic support material is at least one oxide particle size of 15 µm to 300 µm of a metal being Tantalum.

2. The generator according to claim 1, characterized in that the oxide is an oxide having the general formula (1):

$$M_2O_5 \tag{1},$$

wherein M is Tantalum.

3. The generator according to claim 1, characterized in that the oxide is tantalum pentaoxide ($Ta_2O_5$).

4. The generator according to claim 3, characterized in that said $Ta_2O_5$ is present in its alpha- and/or beta-crystalline form.

5. The generator according to claim 1, characterized in that the oxide is obtainable by annealing a metal powder under oxygen atmosphere.

6. The generator according to claim 5, characterized in that the resulting oxide is $Ta_2O_5$.

7. The generator according to claim 1, characterized in that the $^{68}Ge$ parent nuclide is adsorbed to the oxide support material in form of $^{68}Ge(IV)$ cations.

8. The generator according to claim 1, characterized in that the $^{68}Ga$ is eluted from the generator with 0.01 to 0.1 M HCl.

9. The generator according to claim 8, characterized in that the breakthrough of $^{68}Ge$ is $<10^{-5}$%, at an initial activity of 4000 MBq.

10. The generator according to claim 8, characterized in that the elution yield of $^{68}Ga$ is >70% at an initial activity of 3000 MBq.

* * * * *